United States Patent [19]

Castleman

[11] Patent Number: 4,485,499

[45] Date of Patent: Dec. 4, 1984

[54] INTRAOCULAR POSTERIOR CHAMBER LENS

[76] Inventor: Lawrence D. Castleman, 35138 Old Timber Rd., Farmington Hills, Mich. 48018

[21] Appl. No.: 421,215

[22] Filed: Sep. 22, 1982

Related U.S. Application Data

[63] Continuation-in-part of Ser. No. 414,184, Sep. 2, 1982, abandoned.

[51] Int. Cl.³ .............................. A61F 1/16; A61F 1/24
[52] U.S. Cl. ............................................................ 3/13
[58] Field of Search ........................................... 3/13, 1

[56] References Cited

U.S. PATENT DOCUMENTS

| 4,092,743 | 6/1978 | Kelman | 3/13 |
| 4,244,060 | 1/1981 | Hoffer | 3/13 |
| 4,285,072 | 8/1981 | Morcher et al. | 3/13 |
| 4,343,050 | 8/1982 | Kelman | 3/13 |
| 4,377,873 | 3/1983 | Reichert, Jr. | 3/13 |
| 4,412,359 | 11/1983 | Myers | 3/13 |

OTHER PUBLICATIONS

Model PC-11, Posterior Chamber, Manufactured by American Medical Optics, American Hospital Supply Corp., (Advertisement publication), 4 pages, Aug. 1981.

Primary Examiner—Ronald L. Frinks
Attorney, Agent, or Firm—Krass & Young

[57] ABSTRACT

A new type of intraocular posterior chamber lens is provided for implantation in the eye following cataract extraction. The new lens is uniquely structured at its rear face such that, when implanted, a separation or an open zone is provided at the visual axis between the lens body and the posterior capsule so that, in the event of haziness or opacification of the posterior capsule, corrective surgery can later be provided in this open zone means that will allow a corrective or restorative opening to be made in the posterior capsule.

30 Claims, 14 Drawing Figures

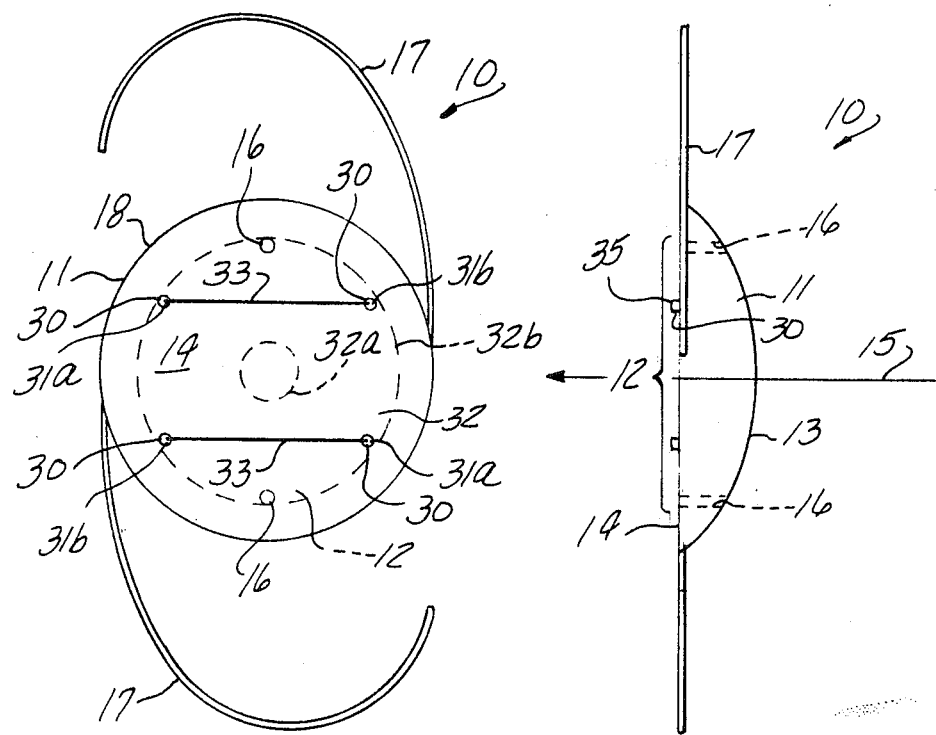
FIG-1
FIG-2
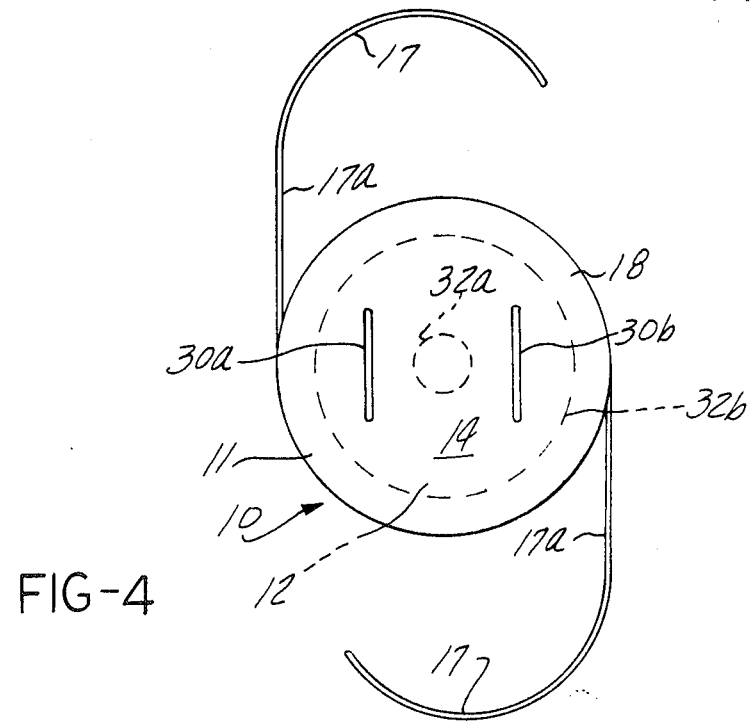
FIG-4

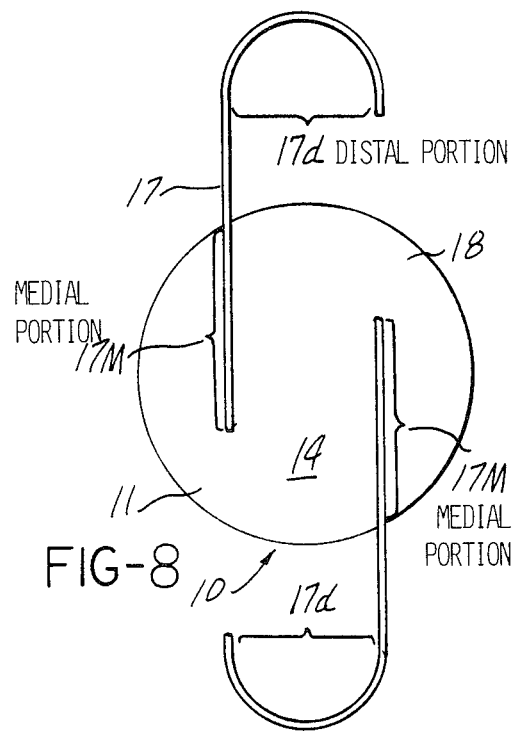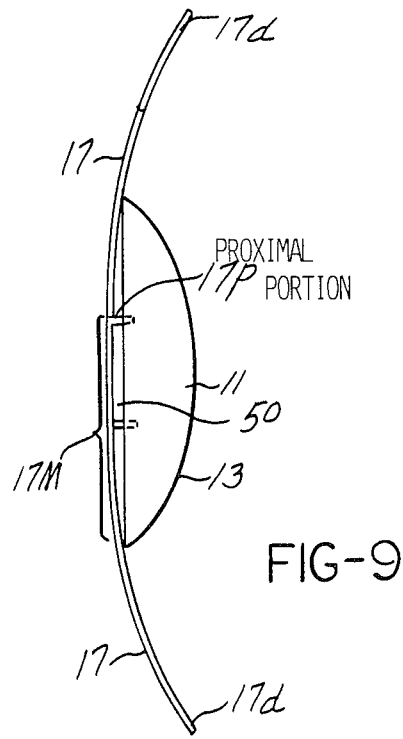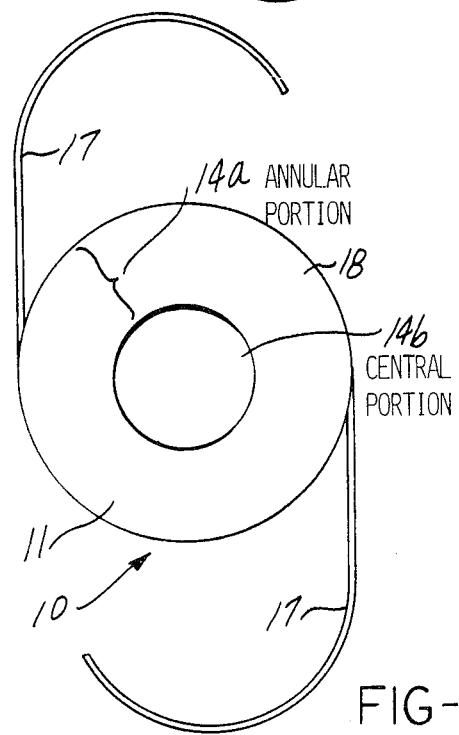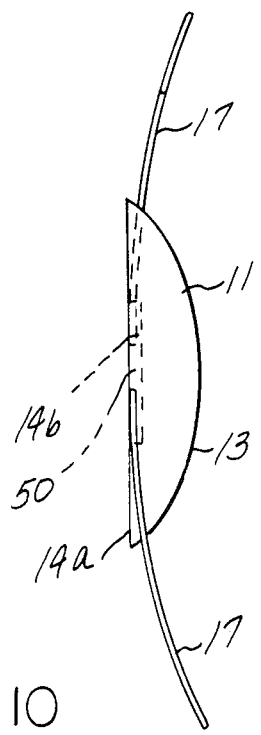

INTRAOCULAR POSTERIOR CHAMBER LENS

CROSS-REFERENCE TO A RELATED APPLICATION

This application is a continuation-in-part of application Ser. No. 414,184, filed Sept. 2, 1982, now abandoned.

TECHNICAL FIELD

This invention relates to artificial body members and, more particularly, to a unique kind of intraocular lens (IOL) intended to be implanted in the posterior chamber of the eye undergoing cataract extraction.

BACKGROUND ART

In the human eye, the lens is situated behind the pupil and iris, and functions to focus light entrant through the cornea and pupil onto the retina at the rear of the eye. The lens is a biconvex, highly transparent structure made of slender, curved rod-shaped ectodermal cells in concentric lamellae surrounded by a thin capsule. The lens capsule is supported at its periphery by suspensory ligaments, called zonules, that are continuous with the ciliary muscle. Contraction of this muscle relaxes the zonules, allowing the lens to become more spherical, thereby altering its focal length.

A cataract condition results when the material within the lens capsule becomes clouded, thereby obstructing the passage of light. To correct this condition, two forms of surgery are used. In intracapsular cataract extraction, the surgeon severs the zonules or suspensory ligaments about the entire periphery of the capsule, and removes the entire lens with the capsule and its content material intact.

In extracapsular cataract extraction, an incision is made through the front wall (the "anterior capsule") of the lens, and the clouded cellular material within the capsule is removed through this opening. Various scraping, suction or phacoemulsification techniques are used to accomplish such extraction. The transparent rear capsule wall (the "posterior capsule") remains in place in the eye. Also remaining in place are the zonules, and peripheral portions of the anterior capsule (the "anterior capsule flaps").

Both intracapsular and extracapsular extraction eliminate the light blockage due to the cataract. However, the light now entrant through the cornea and pupil is totally unfocused since there is no longer a lens in the eye. Appropriate focusing can be achieved by a lens (i.e., a contact lens) exterior to the eye. This approach, though generally satisfactory, has the disadvantage that when the external lens is removed (i.e., when the contact lens is "taken out"), the patient effectively has no sight. A preferred alternative is to implant an artificial lens directly within the eye.

Certain undesirable complications may result from intracapsular surgery. One involves "vitreous loss". The entire region of the eye behind the lens normally is filled with a jelly-like material called the vitreous humor. When the lens is removed intact, the vitreous humor comes through the pupil and may escape from the eye through the incision that was made to accomplish the intracapsular extraction. Adverse side effects can occur.

Another serious complication of intracapsular surgery is called cystoid macular edema (CME). This is an edema or swelling of the macula of the retina. This may be due to certain enzymes which are released from the iris and migrate through the vitreous humor back to the macula, causing swelling. The incidence of both vitreous loss and CME is substantially reduced in the case of extracapsular extraction, since the posterior capsule remains in place and prevents the vitreous humor from reaching the anterior chamber. Thus from the viewpoint of reducing post-surgical complications, extracapsular extraction is preferred.

Various forms of intraocular lenses are known. Generally these fall into two major classes, the anterior chamber lenses which are situated forward of, or mounted to the iris, and posterior chamber lenses which are situated behind the iris and may be mounted either within the ciliary sulcus or groove or within the cleft or fornix of the capsule which remains in place after extracapsular surgery.

One problem associated with the after-use of prior art posterior chamber lenses is secondary cataractic growth, i.e., growth of lens fibers or of capsular fibrosis occurring subsequent to lens implantation. A discussion or surgical procedure for the central posterior capsule may thus be required to eliminate the secondary growth or opacification. Also, although the capsule itself is inanimate, the lens cells living on the capsule are virtually impossible to clean off completely when the cataract extraction is performed. As time goes by, the remaining cells continue to grow and proliferate, forming the glistening, bubbly material called Elschnig's pearls. Seeing is impaired, and discission is required to restore normal sight.

Thus, after extracapsular cataract extraction (ECCE) and intraocular lens implantation, it often becomes necessary to make an opening in the intact posterior capsule. This procedure is difficult when using a posterior chamber lens which has a rear surface, especially a planar or convex rear surface, that seats directly against the posterior capsule. To make the discission the surgeon must insert a knife behind the lens to make the cut. This is difficult to do without displacing the lens or risking rupture of the vitreous face.

One type of posterior chamber lens described by Hoffer in U.S. Pat. No. 4,244,060 is provided at its rear lens surface with an annular lip for spacing the capsule from the edge of the rear face of the lens. The ridge has a special opening to permit, if it should later become necessary, the insertion of a discission instrument behind the edge of the lens as a surgical intervention allowing for corrective removal of post-surgical, secondary capsular ingrowth. However, the mentioned lip structure of the Hoffer lens is not intended to provide for precision microsurgery at a locus defined by the intersection of the visual axis and the microspace at the rear of the lens. Also, with the Hoffer lens, collapse of the posterior capsule directly upon the central portion of the lens rear surface is probable especially in cases where the posterior capsule is flaccid or is under pressure from the vitreous. A further problem exists in identifying the site of the open notch on the posterior of the Hoffer lens since the notch will frequently be obscured from the surgeon's view by the iris.

It is therefore an object of the present invention to provide an improved intraocular posterior chamber lens that overcomes the disadvantages of prior art lenses and uniquely enables subsequent corrective micro-surgery by invasive or non-invasive procedures.

It is another object of the invention to provide an intraocular posterior chamber lens which is specially structured with support members at the rear face and which can readily be implanted.

It is still another object of the invention to provide a new lens of the type described which is designed for permanent implantation and can be serviced in situ by non-invasive surgical procedures.

DISCLOSURE OF THE INVENTION

These and other objects are achieved by providing, for implantation in the posterior chamber of an eye after extracapsular extraction, an intraocular lens having a unique structural configuration at the rear face of the lens, presently to be described, enabling subsequent non-invasive post-operative corrective surgery such as laser surgery, especially Q-switched or mode-locked YAG-laser capsulotomy or other surgery. [See, for example, Staehler et al., Lasers in Surgery and Medicine 1: 191–197 (1980)]. The intraocular lens of the invention comprises a lens body having a central optical region and a rear face, means attached to the lens body for fixating the lens body in operative alignment with the visual axis of the eye, and chamber roof profile defining means including rigid roof support members of predetermined dimension integral with the rear face at diametrically opposed points with respect to a selected portion of the optical region, adapted when the lens is fixated to contact the posterior capsule at support surfaces coinciding with the roof profile and to thereby provide a capsule-covered protected open zone overlying the rear face throughout the selected portion of the central optical region, the dimensions and spacing of the support members being such as to avoid blocking of the visual axis and sagging of the capsule into the open zone between the rear face and thus supported capsule and to thereby enable post-operative non-invasive laser surgery in said open zone. The lens of the invention thus uniquely provides support rearwardly of the lens in the central optical region so that a capsule-covered protected zone is left open indefinitely for the pseudophakic or lens-implanted patient. Consequently, in the event that the patient experiences secondary cataractic growth or other occlusion in the zone whereby sight is impaired, the blockage can be suitably treated and removed non-invasively by conventional laser surgery thus restoring the open optical path through the zone that is essential for pseudophakic vision. The procedure is dimensionally precise so that the lens and posterior capsule are not ionized or otherwise harmed by the radiation, since ionization which destroys the unwanted tissue is confined to the zone circumscribed and protected by the support members of the present lens invention.

The various embodiments of the invention described herein contemplate that posterior fixation of the intraocular lens is accomplished by distal appendage engagement either in the periphery of the ciliary sulcus or the capsular bag or both.

The support members of the lens, according to the invention, are optically invisible. Invisibility is achieved (1) by specially locating the support members so that they are in the optical region but are out of alignment with the visual axis of the eye and/or (2) by restricting the dimensions of the support members so that subjectively they cannot be seen. In one preferred embodiment, the portion of the optical region selected for placement of the support members is an annular segment surrounding the visual axis, defined by a minimum radius of about 0.5 mm. to a maximum radius of about 2.5 mm.

In another aspect, the invention concerns a unique embodiment in which the lens combines a chamber roof structure and a forwardly angulated fixating means that serves to maximize compliance of the posterior capsule with the roof support members. This embodiment in an intraocular lens for implantation in the posterior chamber of an eye after extracapsular extraction, comprises fixating means including forwardly angulated lens-centering appendages each having a distal portion adapted, particularly when implanted by insertion of the distal portion through the pupil, for engagement with the periphery of the posterior chamber, especially within the ciliary sulcus of the eye, and chamber roof profile defining means including rigid roof support members of predetermined opposed points with respect to the optical region, adapted when the lens is fixated to contact the posterior capsule and to thereby provide a capsule-covered protected open zone overlying the rear face of the lens for purposes of enabling non-invasive post-operative laser surgery in said open zone.

More particularly, the latter embodiment comprises a lens body having a central optical region and a rear face; fixating means including forwardly angulated lens-centering appendages each having a distal portion adapted, for purposes of implantation, for insertion through the pupil for engagement with the periphery of the posterior chamber and especially within the ciliary sulcus; and chamber roof profile defining means of predetermined dimension integral with the rear face at diametrically opposed points with respect to the optical region, adapted when the lens is fixated to contact the posterior capsule at support surfaces coinciding with the roof profile and to thereby provide a capsule-covered protected open zone overlying the rear face of the central optical region, the dimensions and spacing of the support members being such as to avoid blocking of the visual axis and sagging of the capsule into the open zone between the rear face and the thus-supported capsule and to thereby enable non-invasive post-operative laser surgery in said open zone.

In another aspect, the invention concerns a unique embodiment of an intraocular lens for implantation in the posterior chamber of an eye after extracapsular extraction, comprising a lens body having a central optical region and a rear face, means proximally attached to the rear face of the lens body for fixating the lens body in operative alignment with the visual axis of the eye, the fixating means including opposed lens centering appendages each have a medial portion and further having a distal portion adapted for engagement with the periphery of the posterior chamber, the medial portion of the appendages being spaced from each other and from a selected portion of the optical region and being adapted when the lens is fixated to contact the posterior capsule and support the capsule in spaced relation from the rear face, thereby providing a capsule-covered protected open zone overlying the rear face throughout the selected portion of the central optical region, the dimensions and spacing of the appendages being such as to avoid blocking of the visual axis and sagging of the capsule into the open zone between the rear face and the thus supported capsule and to thereby enable non-invasive post-operative laser surgery in said open zone. In a preferred embodiment the appendages comprise at least one pair of compressible loop appendages adapted for fixation with the medial portions in substantially parallel relation.

In another preferred embodiment the distal portion of the appendages is forwardly angulated with respect to the rear face of the lens body. Preferably, the forward angulation is in the range from about 5 to about 10 degrees.

In another aspect, the invention concerns the posterior chamber of an eye after extracapsular extraction, comprising a lens body having a central optical region and a rear face, means proximally attached to the lens body for fixating the lens body in operative alignment with the visual axis of the eye, the fixating means comprising lens-centering appendages each having a distal portion adapted for engagement with the periphery of the posterior chamber, the rear face of the lens body having an annular portion and a forwardly offset central portion, the annular rear face portion being adapted when the lens is fixated to contact and support the posterior capsule and the central rear face portion being adapted when the lens is fixated to be spaced from the posterior capsule and to thereby provide a capsule-covered protected open zone overlying the central portion of the rear face of the lens body, the dimensions and spacing of the central portion being such as to avoid blocking of the visual axis and sagging of the capsule into the open zone between the rear face and the thus supported capsule and to thereby enable non-invasive post-operative laser surgery in said open zone.

In one preferred embodiment, the width of the central rear face portion, preferably circular, and preferably comprising a surface that is congruent with the annular portion, is in the range from about 1.5 to about 2.5 mm. The preferred depth of the offset is in the range from about 0.05 to about 0.1 mm. Preferably the distal portion of the appendages is forwardly angulated with respect to the rear face of the lens body. Preferably, the forward angulation is in the range from about 5 to about 10 degrees.

BRIEF DESCRIPTION OF THE DRAWINGS:

The invention will be more fully understood by reference to the following detailed description and accompanying drawings in which:

FIG. 1 is a plan view of a preferred embodiment of an intraocular lens according to the invention;

FIG. 2 is a side view in elevation of the intraocular lens of FIG. 1;

FIGS. 4, 6, 8 and 10 are similar plan views of other preferred embodiments of intraocular lenses according to the invention; and FIGS. 5, 7, 9 and 11, respectively, are side views in elevation of the intraocular lenses of FIGS. 4, 6, 8 and 10.

DESCRIPTION OF PREFERRED EMBODIMENTS AND BEST MODE FOR PRACTICING THE INVENTION

The following description concerns preferred embodiments of the invention, for the purpose of illustrating the invention. Thus, this description is not to be taken in a limiting sense.

Figure 3:
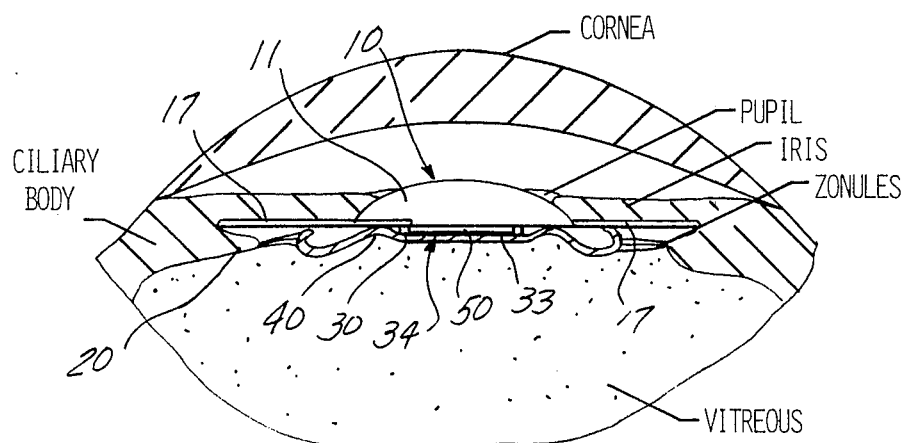
FIG. 3, 3a, 3b and 3c are views in side elevation of preferred embodiments of intraocular lenses in situ, the eye being shown in cross-section.

In the embodiment of FIGS. 1 and 2, the lens 10 includes a lens body 11 having a central optical region 12 with a convex front face 13 and a rear face 14 which is planar, as illustrated, but can be non-planar, shown in alignment with line 15 representing the visual axis of the normal phakic eye. Fenestrations 16 are provided for manipulating, positioning, suturing or fixating the lens in the posterior chamber 20 (FIG. 3). Also, for purposes of positioning and fixation are flexible compressible loops 17 secured by suitable means such as staking (not shown) and extending from the edge 18 of the lens body 11. Support members or pegs 30 integral with and extending from the rear face 14 are provided at diametrically opposed points 31a, 31a and 31b, 31b with respect to the optical region 12, preferably in an annular segment 32 (shown in dotted outline) of the region 12, defined by a minimum radius 32a and a maximum radius 32b. A filament 33, suitably under tension, extending from and joining points 31a and 31b is located on the top of respective pairs of pegs 30. The combination of support pegs 30 and the respective joining filaments 33 as illustrated serves to define a chamber roof profile 34 when the lens is fixated in the eye (as shown in FIG. 3) to contact the posterior capsule 40 at support surfaces which include the peg tops 35 and the topmost surfaces of the joining filaments 33. In preferred embodiments not shown, the 4-peg combination may also include peg-supported filaments 33 which cross each other on the diagonals of the rectangle or may also include such filaments on all four sides of the rectangle or on both sides and diagonals such as to define a chamber roof profile for the capsular support contemplated by the invention.

Figure 5:
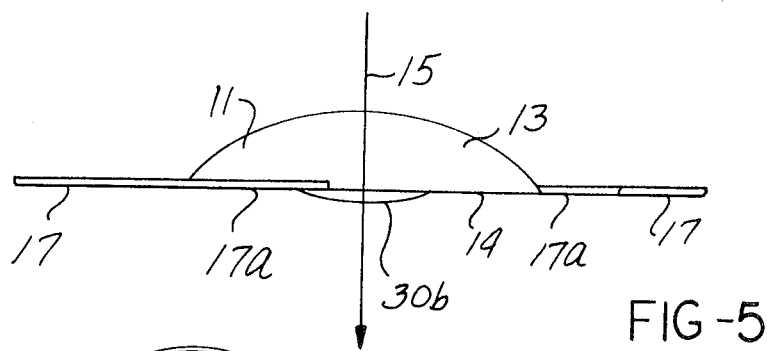
Figure 6:
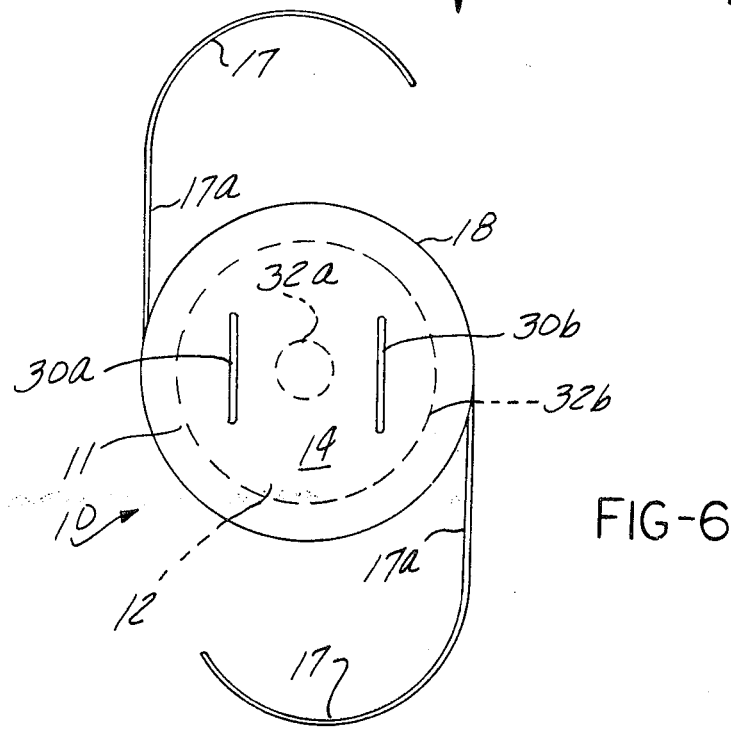

The profile defining means 34 when covered with the capsule 40 provide a protected open zone 50 overlying the rear face 14 throughout the selected portion (that is, within the draped capsular membrane 40 over the rectangle defined by pegs 30) of the central optical region 12. In the preferred embodiment of FIGS. 4 and 5, the lens 10 is generally similar to that of FIGS. 1 and 2 but includes for projecting support members 30 a pair of matching spaced ridges 30a of uniform width that are tapered and have an apex 30b (measuring, as illustrated: lens loop, 12.5 to 14.0 mm., loop to loop/optic of lens, 5.5 to 6.0 mm./ridge length, ca. 3 mm.). The ridges are mutually parallel and preferably also parallel with the base portion 17a of the lens loops 17.

The dimensions and spacings of the projecting support members 30 and filaments 33 are selected such as to avoid blocking of the visual axis 15 and sagging of the capsule into the open zone 50 and to thereby enable non-invasive post-operative laser surgery or microsurgery in the open zone 50 using available technology and equipment, for example, a YAG-neodymium laser of the type available from Meditecs Imports Incorporated, Chevy Chase, Md. 20815. Preferably, the portion of the optical region selected for placement of the support members 30 is the previously mentioned annular segment 32 where the minimum radius is about 0.5 mm. and the maximum radius is about 2.5 mm. The open zone 50 may take any of a variety of shapes consistent with the purposes of the invention. Preferably, the height of the open zone 50, particularly for optimum spacing and positioning purposes, is in the range from about 0.1 to about 0.6 mm. The support members 30 may take any of a variety of shapes consistent with the purposes of the invention. Preferably, for optical clarity, the thickness of the support members 30 is not more than about 0.1 mm. Preferred shapes are pegs or ridges, as described. The open zone 50 may take the shape afforded by the draped capsule 40 on a single peg 30 or ridge 30a. Preferably, the support members comprise either spaced pegs 30 joined by filament means 33 or mutually parallel spaced filament or ridge means 30a which ridge means may be straight or tapered, the diametrical spacing of the support members being from about 1 to about 4 mm.

It is a feature of the invention that the unique design of the lens enables the lens to be inserted and implanted using presently available techniques (see, for example, Langston, Intraocular Lens Implantation, 137 et seq., Little, Brown and Co., Boston, 1982) without special equipment or training. In other words, the chamber roof profile defining structure at the rear face of the lens body can readily be accommodated through the incision during insertion without hang-up or other complications. Further, the mentioned structure is compatible with unimpaired vision through the visual axis by virture of spacing and low cross-section. The lens including the body, lens loops or functionally equivalent appendages, and support members can be of conventional material and construction. For example, the lens body and support structures can be lathed, injection molded, or otherwise worked or formed from medical grade polymethylmethacrylate (PMMA, PERSPEX® CQ) or equivalent material. The lens loops can likewise be fabricated from suitable material, e.g., transparent or colored polypropylene (PROLENE®). The support structures can be similarly made from PMMA or transparent polypropylene. The latter material is especially suitable, for example, for the pegs and ridges (which may be formed individually and press-fitted or otherwise fastened or inserted into fine holes machined into the lens body) and for the filaments (e.g., 12-0 transparent).

Figure 3A:
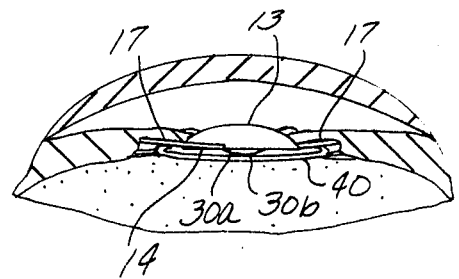
Figure 7:
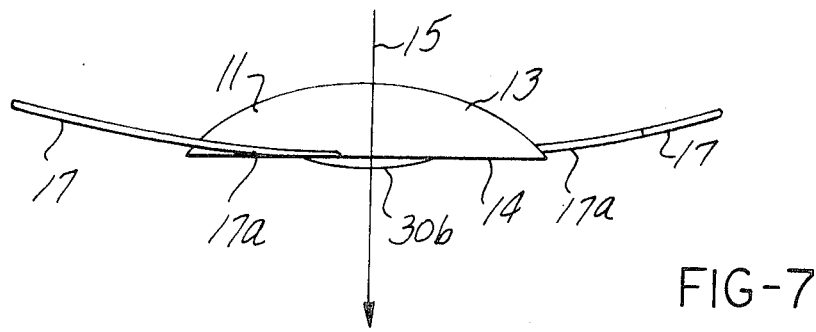

The intraocular lens of the types illustrated in FIGS. 7, 9 and 11 is configured with a forward angulation of the appendages or flexible loops 17 preferably with each appendage extending at a forward angle in the range from about 5 to about 10 degrees with respect to the plane of the lens. Thus, when implanted in the posterior chamber (as seen in FIG. 3a) the distal ends of the appendages are located for fixation primarily in the periphery of the ciliary sulcus (however, the distal ends can be located in the periphery of the capsular bag or periphery of both sulcus and capsular bag). The front face 13 is centered behind and closely in contact with the iris, and the rear face 14 is presented for supporting contact at support members 30, 30a and 30b with the posterior capsule 40, the particular relationship of the forwardly angulated appendages and posterior capsule favoring the stretching of the capsule over the support members to tend to make the capsule taut and thereby avoiding possible sagging of the capsule into the open zone 50. The forward angulation serves also to facilitate intrapupillary insertion and correct placement of the appendages. In particular, when the lens is inserted into the aphakic eye through a corneal incision, the distal end of one appendage can be threaded through the incision and the pupil for placement radially outward preferably to the periphery of the ciliary sulcus rather than the periphery of the posterior capsule. The distal end of the remaining one or more forwardly angulated appendages for the lens can then be inserted precisely and selectively into the opposing sulcus, with appropriate flexing and manipulation to achieve centering of the lens body behind the iris with its rear face contacting the posterior capsule at points located outside of the open zone 50.

The invention contemplates that fixation may be accomplished by means of any lateral opposed compressible appendage support structures that may be per se conventional and that are suitable for posterior chamber lens fixation, especially open or closed loop appendages, preferably J-loops, preferably loop pairs, and more preferably superior and inferior loops. For purposes of locating the lens body on center, the opposed appendages can have any of various matched or unmatched configurations and compressibilities consistent with the objectives of long term comfort and reliability.

Figure 3B:
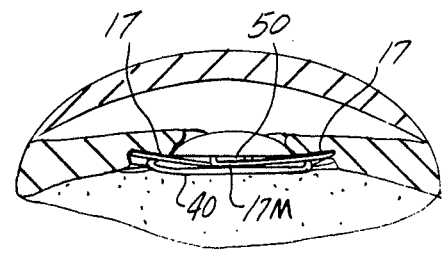
Figure 3C:
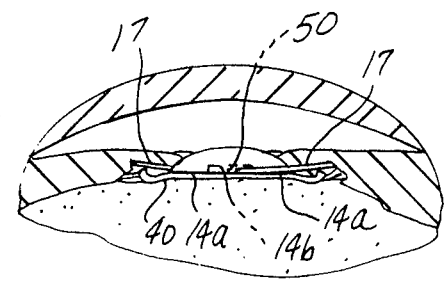

Preferred embodiments of the unique intraocular lens are shown in FIGS. 8 and 10. The lens 10 includes a lens body 11 with front and rear faces and a pair of proximally attached appendages 17. As shown in FIG. 8, the appendages are attached by the proximal portion 17p to the rear face 14 at diametrically opposed points. As seen in FIG. 9, the proximal portion 17p is staked into the lens body. The proximal portion 17p serves to give the lens body support for fixation purposes and also to space the medial portion 17m from the rear face 14, particularly at the center of the rear face to provide there an open zone 50 at and near the visual axis 15. For purposes of peripheral attachment within the posterior chamber, the appendages extend outwardly and forwardly from the medial portion 17m to the distal portion 17d. Thus, when the lens is inserted and fixated as seen in FIG. 3b, the posterior capsule 40 is supported by the medial portions 17m in spaced relation from the rear face 14 (which can be maximized by forward angulation of the appendages) leaving therebetween an open zone 50 of suitable depth preferably from about 0.5 to about 2.5 mm. deep. By these means the implanted lens uniquely enables secondary non-invasive laser microsurgery within the open zone that can clear the visual axis of occluding disease sites. Similarly as shown in FIG. 10, the structure at the rear face of the lens provides an open zone 50 that enables non-invasive surgery while implanted; the rear face is in two parts: an annular portion 14a and a central portion 14b. The rear face can have a given surface (e.g., planar or convex) and as shown the central portion is forwardly offset from, and generally congruent with, the annular portion. Thus when the implanted lens body is contacted by the posterior capsule 40 as seen in FIG. 3c, such contact is made at the supporting annular portion 14a so that especially with stretching, the capsule bridges the central portion 14b (maximized by forward angulation of the appendages 17), leaving an open zone 50 of suitable depth. The open zone in turn uniquely enables any secondary non-invasive laser microsurgery that may be elected or required.

What is desired to claim as my exclusive property in the invention, as described, is the following:

1. An intraocular lens for implantation in the posterior chamber of an eye after extracapsular extraction, comprising:

a lens body having a central optical region and a rear face, means comprising lens-centering appendages each having a base portion attached to the lens body for fixating the lens body in operative alignment with the visual axis of the eye, and chamber-roof profile defining means including rigid roof support members comprising parallel spaced ridge means that are substantially parallel with the base portion of the lens-centering appendages, of predetermined dimension integral with the rear face at diametrically opposed points with respect to a selected portion of the optical region, adapted when the lens is fixated to contact the posterior capsule at support surfaces coinciding with the roof profile and to thereby provide a capsule-covered protected open zone overlying the rear face throughout the selected portion of the central optical region, the dimensions and spacing of the support members being such as to avoid blocking of the visual axis and sagging of the capsule into the open zone between the rear face and the thus supported capsule and to thereby enable non-invasive post-operative laser surgery in said open zone.

2. An intraocular lens according to claim 1 where the portion of the optical region selected for placement of the support members is an annular segment in the optical region surrounding the visual axis defined by a minimum radius of about 0.5 and a maximum radius of about 2.5 mm.

3. An intraocular lens according to claim 1 where the support members comprise tapered ridge means.

4. An intraocular lens according to claim 1 where the support members comprise parallel spaced tapered ridge means.

5. An intraocular lens according to claim 1 where the support members are diametrically spaced at a distance in the range from about 1 to about 4 mm.

6. An intraocular lens according to claim 1 where the maximum height of the open zone is in the range from about 0.1 to about 0.6 mm.

7. An intraocular lens according to claim 1 where the thickness of the support members is not more than about 0.1 mm.

8. An intraocular lens according to claim 1 where the support members comprise a pair of parallel diametrically spaced tapered ridges each having a maximum height of about 0.3 mm.

9. An intraocular lens for implantation in the posterior chamber of an eye after extracapsular extraction, comprising:
a lens body having a central optical region and a rear face,
means proximally attached to the lens body for fixating the lens body in operative alignment with the visual axis of the eye, the fixating means comprising forwardly angulated lens-centering appendages each having a base portion and a distal portion adapted for engagement with the periphery of the posterior chamber, and
chamber-roof profile defining means including rigid roof support members comprising parallel spaced ridge means that are substantially parallel with the base portion of the lens-centering appendages of predetermined dimension integral with the rear face at diametrically opposed points with respect to the optical region, adapted when the lens is fixated to contact the posterior capsule at support surfaces coinciding with the roof profile and to thereby provide a capsule-covered protected open zone overlying the rear face of the central optical region, the dimensions and spacing of the support members being such as to avoid blocking of the visual axis and sagging of the capsule into the open zone and to thereby enable non-invasive post-operative laser surgery in said open zone.

10. An intraocular lens according to claim 9 where the distal portion of the appendages is adapted for engagement within the ciliary sulcus of the eye.

11. An intraocular lens according to claim 9 where the support members comprise tapered ridge means.

12. An intraocular lens according to claim 9 where the support members are diametrically spaced at a distance in the range from about 1 to about 4 mm.

13. An intraocular lens according to claim 9 where the maximum height of the open zone is in the range from about 0.1 to about 0.6 mm.

14. An intraocular lens according to claim 9 where the thickness of the support members is not more than about 0.1 mm.

15. An intraocular lens according to claim 9 where support member comprises at least one ridge having a maximum height in the range from about 0.1 to about 0.4 mm.

16. An intraocular lens according to claim 15 where the support members comprise a pair of parallel diametrically spaced tapered ridges each having a maximum height of about 0.3 mm.

17. An intraocular lens according to claim 9 where the optical region support members are located in an annular segment in the optical region surrounding the visual axis defined by a minimum radius of about 0.5 and a maximum radius of about 2.5 mm.

18. An intraocular lens according to claim 9 where each appendage comprises a compressible loop.

19. An intraocular lens according to claim 9 where each appendage extends forwardly at an angle in the range from about 5 to 10 degrees.

20. An intraocular lens for implantation in the posterior chamber of an eye after extracapsular extraction, comprising:
a lens body having a central optical region and a rear face,
means attached to the lens body for fixating the lens body in operative alignment with the visual axis of the eye, and
chamber-roof profile defining means including rigid roof support members comprising spaced pegs joined by filament means, of predetermined dimension integral with the rear face at diametrically opposed points with respect to a selected portion of the optical region, adapted when the lens is fixated to contact the posterior capsule at support surfaces coinciding with the roof profile and to thereby provide a capsule-covered protected open zone overlying the rear face throughout the selected portion of the central optical region, the dimensions and spacing of the support members being such as to avoid blocking of the visual axis and sagging of the capsule into the open zone between the rear face and the thus supported capsule and to thereby enable non-invasive post-operative laser surgery in said open zone.

21. An intraocular lens according to claim 20 where the support members comprise a pair of diametrically peg-supported spaced filaments.

22. An intraocular lens according to claim 20 where the support members comprise parallel spaced filament means.

23. An intraocular lens for implantation in the posterior chamber of an eye after extracapsular extraction, comprising:
a lens body having a central optical region and a rear face,
means proximally attached to the lens body for fixating the lens body in operative alignment with the visual axis of the eye, the fixating means comprising lens-centering appendages each having a distal portion adapted for engagement with the periphery of the posterior chamber, and chamber-roof profile defining means including rigid roof support members of predetermined dimension integral with the rear face at diametrically opposed points with respect to the optical region, the support members comprising a pair of diametrically spaced end-supported filaments, adapted when the lens is fixated to contact the posterior capsule at support surfaces coinciding with the roof profile and to thereby provide a capsule-covered protected open zone overlying the rear face of the central optical region, the dimensions and spacing of the support members being such as to avoid blocking of the visual axis and sagging of the capsule into the open zone and to thereby enable non-invasive post-operative laser surgery in said open zone.

24. An intraocular lens for implantation in the posterior chamber of an eye after extracapsular extraction, comprising:

a lens body having a central optical region and a rear face, means proximally attached to the rear face of the lens body for fixating the lens body in operative alignment with the visual axis of the eye, the fixating means including opposed lens centering appendages each having a medial portion and further having a distal portion adapted for engagement with the periphery of the posterior chamber, the medial portion of the appendages being dimensioned to extend laterally across the rear face more than half the lateral dimension thereof and being spaced from each other and from a selected portion of the optical region and being adapted when the lens is fixated to contact the posterior capsule and support the capsule in spaced relation from the rear face thereby providing a capsule-covered protected open zone overlying the rear face throughout the selected portion of the central optical region, the dimensions and spacing of the appendages being such as to avoid blocking of the visual axis and sagging of the capsule into the open zone between the rear face and the thus supported capsule and to thereby enable non-invasive post-operative laser surgery in said open zone.

25. An intraocular lens according to claim 24 where the appendages comprise at least one pair of compressible loops having substantially parallel medial portions.

26. An intraocular lens according to claim 24 where the distal portion of the appendages is forwardly angulated with respect to the rear face of the lens body.

27. An intraocular lens according to claim 26 where the forward angulation is in the range from about 5 to about 10 degrees.

28. An intraocular lens for implantation in the posterior chamber of an eye after extracapsular extraction, comprising:

a lens body having a central optical region and a rear face, means proximally attached to the lens body for fixating the lens body in operative alignment with the visual axis of the eye, the fixating means comprising lens-centering appendages each having a distal portion forwardly angulated with respect to the rear face of the lens body and adapted for engagement with the periphery of the posterior chamber, the rear face of the lens body having an annular portion and a second forwardly offset central portion, the annular rear face portion being adapted when the lens is fixated to contact and support the posterior capsule and the central rear face portion being adapted when the lens is fixated to be spaced from the posterior capsule and to thereby provide a capsule-covered protected open zone overlying the central portion of the rear face of the lens body, the dimensions and spacing of the central portion being such as to avoid blocking of the visual axis and sagging of the capsule into the open zone between the rear face and the thus supported capsule and to thereby enable non-invasive post-operative laser surgery in said open zone.

29. An intraocular lens according to claim 28 where the forward angulation is in the range from about 5 to about 10 degrees.

30. The intraocular lens of claim 23 wherein the filaments each include a section intermediate their ends which extends parallel to and spaced from the rear face of the lens.

* * * * *